United States Patent [19]

Mulshine et al.

[11] Patent Number: 5,455,159

[45] Date of Patent: Oct. 3, 1995

[54] METHOD FOR EARLY DETECTION OF LUNG CANCER

[76] Inventors: James L. Mulshine, 7719 Savannah Dr., Bethesda, Md. 20817; Melvyn S. Tockman, 202 Kemble Rd., Baltimore, Md. 21218; Prabodh K. Gupta, 7 Lockmoor Ct.; John K. Frost, 1004 Brooklandwood Rd., both of Lutherville, Md. 21093

[21] Appl. No.: 152,881

[22] Filed: Nov. 16, 1993

Related U.S. Application Data

[63] Continuation of Ser. No. 747,502, Aug. 19, 1991, abandoned, which is a continuation of Ser. No. 177,465, Apr. 4, 1988, abandoned.

[51] Int. Cl.⁶ .................. G01N 33/574; G01N 33/53; G01N 33/577
[52] U.S. Cl. .................. 435/7.23; 435/7.9; 435/7.92; 436/64; 530/388.8
[58] Field of Search .................. 435/7.23, 7.9, 435/7.92; 436/63, 813, 64; 530/388.8

[56] References Cited

U.S. PATENT DOCUMENTS

| | | | |
|---|---|---|---|
| 4,569,788 | 2/1986 | Mulshine et al. | 435/7 |
| 4,624,930 | 11/1986 | Tanswell et al. | 436/500 |
| 4,683,200 | 7/1987 | Hirohashi et al. | 435/68 |
| 4,690,890 | 9/1987 | Loor et al. | 435/7 |
| 4,731,326 | 3/1988 | Thompson et al. | 435/7 |
| 4,737,579 | 4/1988 | Hellstrom et al. | 436/548 |
| 4,782,015 | 11/1988 | Allison et al. | 436/548 |
| 4,800,155 | 1/1989 | Taniguchi et al. | 436/548 |
| 4,816,402 | 3/1989 | Rosen et al. | 436/548 |
| 4,865,998 | 9/1989 | Felckert et al. | 436/548 |
| 4,873,188 | 10/1989 | Hellström et al. | 435/7 |
| 4,886,745 | 12/1989 | Morhenn | 435/7 |

OTHER PUBLICATIONS

Roitl, "Essential Immunology", Fifth Ed. (1984) 156–157. (Blackwell Scientific Publ., Oxford).
Rosen, S. T. et al. "Cancer Research", vol. 44 (1984) 2052–2061.
Doyle, et al. "J. Exp. Medicine", vol. 161 (1985) 1135–1157.
Fargion et al. Cancer Research, vol. 46, May 1986, pp. 2633–2638.
Cuttitta et al, Proc. Natl. Acad. Sci. U.S.A., vol. 78, 1981, pp. 4591–4595.
Ball et al, JNCL, vol. 72, 1984, pp. 593–599.

Primary Examiner—Toni R. Scheiner
Assistant Examiner—Nancy J. Parsons
Attorney, Agent, or Firm—Cushman, Darby & Cushman

[57] ABSTRACT

The present invention relates to a method for early detection of lung cancer. The method comprises obtaining samples from the body, especially respiratory tract material including sputum or bronchial fluid or any other pulmonary tissue or thoracic cells or regional lymph nodes, and assaying the samples with monoclonal antibodies for the presence of antigens whose enhanced presence correlates with the development of lung cancer. The method of the present invention permits identification of lung cancer up to two years prior to the development of clinical lung cancer, and thus enables early treatment of the lung cancer.

7 Claims, No Drawings

METHOD FOR EARLY DETECTION OF LUNG CANCER

This is a continuation of patent application Ser. No. 07/747,502, filed on Aug. 19, 1991, now abandoned, which was abandoned; which is a continuation of patent application Ser. No. 07/177,465 filed Apr. 4, 1988, now abandoned.

FIELD OF THE INVENTION

The present invention relates to the early diagnosis of cancer; and more particularly, to a method and assay kit for early detection of lung cancer.

BACKGROUND OF THE INVENTION

Lung cancer remains the major cause of cancer death among both males and females. Recognition of the expression of one or more neoplastic antigens in advance of clinical cancer opens several potential therapeutic alternatives.

Four types of lung cancer are found in humans: squamous, adeno, small cell, and large cell. Each tumor expresses specific differentiation features or surface phenotype determinants, all of which distinguish these cells from normal cells. The development of monoclonal antibody diagnostic techniques has greatly enhanced the production of reagents capable of differentiating normal cells from cancer cells and differentiating types of cancer cells from other cancer cells.

Sputum cytology screening of bronchial epithelial-cell morphologic atypia has not so far led to frequent, early-stage lung cancer detection and cure. This was most convincingly demonstrated in a large three-institution study sponsored by the National Cancer Institute, as reported in *Am Rev Respir Dis* 130:545–549, 555–560, 561–565, and 565–570, 1984. As part of this study to determine whether the addition of sputum cytology screening could significantly enhance lung cancer detection and reduce lung cancer mortality when compared to radiographic screening alone, the Johns Hopkins Lung Project obtained expectorated sputum cytology specimens and chest radiographs serially over a period of from five to eight years from male smokers, 45 years of age and older. From 1973 to 1977, 10,384 of these high risk individuals were recruited. Half were randomized to receive cytology screening plus chest radiography, and the other half were screened by radiography alone. Cytology screening was found to be insufficiently sensitive, there being too many false negatives.

Several mouse monoclonal antibodies produced against antigens on small cell and non-small cell human lung cancer have been used in immunohistochemical assays to study tumor biology, lung cancer immunolocalization, and to give clues to tumor ancestry. The antigens recognized by these antibodies are expressed on a variety of tumors as well as normal fetal tissue. As summarized in the proceedings of the First International Workshop on Antigens of Small Cell Lung Cancer, Souhami et al., *Lancet* 2(8554): 325–6, 1987, there are nearly 100 monoclonal antibodies being investigated to study small cell and non-small cell cancer of the lung. This workshop supported central registry coding of antibodies followed by blinded staining of a variety of normal and neoplastic tissues. Statistical analyses of the results led to a definition of clusters of reactivity which suggested similar antigenic determinants were being recognized by two or more monoclonal antibody reagents. None of the antigens studied were either specific for small cell lung cancer or were universally present on all small cell lung cancer specimens studied.

Rather than strict tumor markers, these antigenic determinants may be markers of differentiation. Progressive neoplastic differentiation in carcinogen exposed individuals may lead to an increased expression of these markers in the bronchial epithelium before overt development of a pulmonary neoplasm.

Mulshine et al, in U.S. Pat. No. 4,569,788, disclose monoclonal antibodies which can be used to detect human non-small cell lung cancer and distinguish this type of cancer from all other types of lung cancer and normal tissue cells. These two antibodies may be utilized in kit form to distinguish non-small cell lung cancer form other forms of lung cancer by testing the tumor tissue.

Among other monoclonal antibodies used to determine cancer in humans is a monoclonal antibody of the IgM class, U.S. Pat. No. 4,683,200, to Hirohashi et al. The monoclonal antibody disclosed in this patent is reactive with human cancers of the lung, and can be used for serum diagnosis of a patient suffering from cancer.

Loor et al, U.S. Pat. No. 4,690,890, disclose a process for detecting at least two antigens using an immunometric dual sandwich assay containing an effective amount of at least one monoclonal antibody against each antigen. This technique is particularly useful for assaying for prostatic acid phosphatase and prostate antigen.

Tanswell et al, U.S. Pat. No. 4,624,930, disclose a process for determining the presence of polyvalent antigens by incubation with three receptors wherein the first receptor is a complete antibody or an antibody covalently bound to hapten, the second receptor is an antibody which is capable of binding with only a part of the first receptor, and the third receptor, which must not cross-react with the second receptor, can be an antibody capable of binding with the antigen, which is obtained from an animal species different from that from which the first receptor is obtained.

SUMMARY OF THE INVENTION

It is an object of the present invention to overcome deficiencies in the prior art, such as indicated above.

It is another object of the present invention to provide for early diagnosis of lung cancer.

It is yet another object of the present invention to provide a kit and a technique for use in early diagnosis of lung cancer.

According to the present invention, lung cancer can be detected at a much earlier stage than has previously been possible, in some cases more than two years earlier than with any other assay method, by using monoclonal antibodies to detect cells that express antigens whose enhanced presence correlates with the development of lung cancer. The process of the present invention comprises assaying for the presence of antigens in bronchial fluid or sputum, using antibodies which recognize tumor associated antigens, differentiation antigens, Class I or II antigens, or any antigen differentially expressed on normal bronchial cells versus dysplastic bronchial cells versus neoplastic bronchial cells. This method has been found to be far more sensitive in detecting lung cancer than any previous assaying methods, including the John Hopkins study reported, supra.

The detection systems that can be used in the process according to the present invention include standard immunometric detection systems, including ELISA, cell sorting or fluorescence Activated Cell sorting assays, Western blotting assays, immunoprecipitation assays, colorimetric or densitometry based assays, and the like.

Using the technique of the present invention, murine monoclonal antibodies to a glycolipid antigen of small cell and a protein antigen of non-small cell lung cancer were applied to preserved sputum specimens from individuals who participated in the Johns Hopkins Lung Project, which project is described supra.

In that study, which was originally undertaken to evaluate the efficacy of sputum cytology screening, half of the high risk participants (5226 males of at least 45 years of age, currently smoking at least one pack of cigarettes per day) were randomly assigned to produce specimens for cytopathological analysis. During regular screenings over the next five to eight years, 626 (12%) showed moderate or greater atypia. Sixty-nine of these (26 who progressed to cancer, 43 who did not) were randomly selected for a blind improved monoclonal antibody immunostaining protocol. Satisfactory specimens with morphologic atypia immunostained positively in 14 of the 22 patients who eventually progressed to cancer (sensitivity 64%), and were non-reactive in 35 of the 40 patients who did not progress to lung cancer (specificity 88%). Review of the false negative atypias, failure to stain, showed that they were collected an average of 57 months preceding a diagnosis of cancer. In contrast, the true positive specimens had been collected 24 months prior to diagnosis. Later specimens, an average of 26 months prior to cancer, from those which were originally false negative, did stain positively, improving the sensitivity to 91%. The specificity among truely negative specimens collected from individuals who had not developed lung cancer during seven to eight years of follow-up screening was 88%.

Thus, the assay method of the present invention, using samples collected in a previous three-institute study, identified lung cancer in patients up to two years before these patients developed clinical symptoms of lung cancer. This assay method was far more sensitive than the methods used in the previous study in detecting lung cancer in the very early stages. Recognition of neoplastic antigen expression two years in advance of clinical cancer may thus be a valuable intermediate endpoint in studies of lung cancer prevention, detection, and therapy.

DETAILED DESCRIPTION OF THE INVENTION

According to the present invention, antibodies are used to detect cells in bronchial fluid or sputum that express antigens whose enhanced presence correlates with the development of lung cancer. The assay is particularly useful for patients who are at risk for lung cancer, including smokers, workers who have been exposed to asbestos, and the like. The assays may be of any conventional type of immunoassay, including ELISA, radioimmunoassay, fluorescence immunoassay, chemiluminescence immunoassay, cell sorting or fluorescence activated cell sorting assays, Western blotting techniques, immunoprecipitation assays, colormetric or densitometry based assay, and the like.

The cytology screening as described above consisted of a sputum induction with either a 25-minute inhalation of ultrasonically aerosolized balanced salt solution (Hanks BSS) or a 15-minute inhalation of hypertonic saline. Aliquots of the resulting sputum were smeared on glass slides for Papanicolaou staining and interpretation. The remaining material was homogenized, concentrated, and placed in Saccomanno's preservative solution (SPS, 2% polyethylene glycol in 50% ethanol) using standard methods, as described in Saccomanno et al., *Acta Cytol* 2:305–10, 1963. Slides were also prepared for Papanicolaou staining from the SPS-preserved material. At four months and again at eight months following induction, a jar of SPS was mailed to these participants. For the next three mornings, sputum was expectorated into the jar containing the SPS, and this combined specimen was mailed back to the laboratory for cytologic analysis.

As has been previously described, 5226 men has been allocated to receive cytologic screening. During the course of the project, 626 (12%) of these participants had moderate or greater atypia on one or more of their specimens, excluding upper airways cancers and metastases form extra-thoracic primaries. Individuals with at least moderate atypia in their sputum cytology underwent a second sputum induction. All such specimens were placed in SPS and stored for future investigation.

The first atypical cytology specimens of these 626 participants were divided into four groups, as shown in Table 1. Two of the groups consisted of participants whose sputum demonstrated moderate atypia on two screenings: 537 (86%) of these never developed lung cancer, Group I, and 40 (6.4%) progressed to lung cancer, Group II. All four major lung cancer cell types were represented in Group II: 12 squamous, 9 small cell, 7 adeno, 8 large cell, and 4 others or mixed.

Groups III and IV consisted of those participants with marked atypia on at least two occasions. Group III consisted of three individuals (0.5%) who never progressed to cancer. Group IV consisted of 46 individuals (7.4%) who progressed to non-small cell cancer; 41 developed squamous, three adenocarcinoma, and two developed large cell cancer. There were no small cell cancers in this category. In fact, all of the small cell cancers that were detected in the Johns Hopkins Lung Project study were either detected by radiography or came to clinical attention between screenings.

TABLE 1

| Allocation of JHLP Participants with Stored Sputum Specimens by Severity of atypia and Development of Lung Cancer |
| --- |
| 626 (100%) Moderate Atypia |
| 537 (86%) Group I Atypia < Marked (× 2) |
| No Lung Cancer |
|   40 (6.4%) Group II Atypia < Marked (× 2) |
|   12 Squamous |
|    9 Small Cell |
|    7 Adeno |
|    8 Large Cell |
|    4 Other, mixed |
|    3 (0.5%) Group III Atypia >= Marked (× 2) |
| No Lung Cancer |
|   46 (7.4) Group IV Atypia >= Marked (× 2) |
|   41 Squamous |
|    3 Adeno |
|    2 Large Cell |

From the total of 626 specimens, samples from these four groups were randomly selected to be immunostained. The sampling fractions are shown in Table 2. Of the 537 who did not go on to cancer, Group I, 40, with an average of 96.8 months of follow-up, range 34 to 142 months, were randomly selected. Of those who progressed to cancer, 40 in Group II, 46 in Group IV, subjects were randomly selected from each cell type stratum, 15 and 11 from Groups II and IV, respectively. All of the three cases form Group III (marked atypia that did not progress to cancer) were selected. These procedures resulted in the selection of a total of 69 cases which were then coded for the blinded monoclonal antibody immunostaining protocol described below.

TABLE 2

| | Sampling Fractions | | |
|---|---|---|---|
| | n | Selected | % |
| Group I* | 537 | 40 | 7.4 |
| Group II° | 40 | 15 | 37.5 |
| Group III | 3 | 3 | 100.0 |
| Group IV° | 46 | 11 | 23.9 |

The characteristics of the NCI-Navy Medical Oncology Branch monoclonal antibodies with specificity for a glycolipid antigen of small cell cancer (code numbers 534F8, 600A6, and 624H12) and a protein antigen of non-small cell cancer (code numbers 703D4, and 704A1) have been previously reported, cf. Fargion et al., *Cancer Res* 46:2633–2638, 1986; Mulshine et al., *J. Immunol* 131:497–502, 1983; Rosen et al., *Cancer Res* 44:2052–2061, 1984; Spitalnik et al., *Cancer Res* 46:4751–4755, 1986. One SCC Mab (624H12) and one NSCC Mab (703D4) were selected for this study; the NSCC monoclonal antibodies are the subject of U.S. Pat. No. 4,569,788, and are incorporated herein by reference. Biotinylated anti-rat IgM was purchased from Zymed Laboratories (South San Francisco, Calif.); biotinylated anti-mouse IgG, -horse IgG, -rabbit IgG, and Avidin-Biotin-Peroxidase Complex (ABC) reagents were all purchased from Vector Laboratories (Burlingame, Calif.).

Small cell cancer (SCC) and non-small cell cancer (NSCC) lung tumor cells from cell lines maintained at the Johns Hopkins Oncology Center were preserved in SPS and used as positive controls. Sputum specimens and control cells, each stored in SPS, were resuspended by brief vortexing, then deposited on glass slides using a Cytospin centrifugation apparatus purchased from Shandon Southern Instruments (Sewickley, Pa.).

Since the variability from one "run" to the next could potentially affect the overall results of the study, multiple slides of each sputum specimen were stained to minimize the effects of staining variability. In many cases, ten slides were stained; five with each of the two (SCC and NSCC) antibodies. Individual specimens were also evaluated for potential cross-reactivity with SCC and NSCC antibodies by staining at least one slide of each specimen with each of the two antibodies separately.

A complete description of the staining protocol used in this procedure is contained in Gupta et al., *Diag Cytopathol* 1:133–136, 1985. Throughout the procedure, the slides were washed in phosphate buffered saline, 0.01M at pH 7.4, using a magnetic stirrer at its lowers setting. All incubations took place in a sealed, humidified chamber at room temperature (25° C.). Briefly, the immunostaining procedure involved application of a marker-specific primary antibody solution, followed successively by a biotinylated secondary antibody solution (directed against the species/subclass of immunoglobulin in which the primary antibody was raised), a biotinylated tertiary antibody solution (directed against the second antibody), the Avidin-Biotin-Complex (ABC) reagent, and finally the substrate-chromogen solution (0.01% hydrogen peroxide and 0.05% diaminobenzidine in PBS). Specimens were then counterstained with 0.125% methylene blue and mounted by routine methods.

The completed preparations were independently evaluated by two observers who were unaware of whether or not the specimen had been produced by a participant who subsequently developed lung cancer. The results were recorded on specially designed report forms which contained the coded identification and a means for recording data pertinent to the technical aspects of the protocol, such as the antibody and control specimen used; the number and type of epithelial (atypical and neoplastic) and inflammatory cells; and the qualitative and quantitative features of positively-stained cells.

Staining intensity was graded independently by the two observers using a scale which ranged from negative to equivocal (±) to strongly positive (4+), compared to the positive control. The immunocytochemical reactivity of each lung cancer case with either set of monoclonal antibodies (anti-SCC and anti-NSCC) was determined by dividing the sum of the scores given for each preparation by the total number of preparations for each specimen. Only staining intensities of 2+ or greater were considered unequivocally positive. Negative specimens were defined as those which contained atypical cells that did not stain with a 2+ intensity. The complete absence of tumor or atypical cells, the presence of obscuring quantities of inflammatory cells, the presence of excessive levels of nonspecific "background" staining or nonspecific staining of the entire slide were considered grounds for scoring a specimen as unsatisfactory, cf. Table 3.

TABLE 3

Staining Definitions

I. Unsatisfactory
   Specimen Quality (preserved 4–8 yr)

1. Contains only non-pulmonary material
   2. Excessive inflammation
   3. Excessive cellular degeneration
   4. Pulmonary material without atypical cells
   Technical 1. Excessive "background" staining
   2. Complete lack of any staining
II. Negative Atypical cells present in specimen but not staining
III. Positive Stain >= 2+/4+

Of the 69 specimens selected, 26 specimens had been obtained from participants who progressed to lung cancer. Four of these (15%) were unsatisfactory, not significantly different from the proportion (7%) of unsatisfactory staining specimens which was found among the 43 participants that did not progress to lung cancer, as shown in Table 4. The Participants with unsatisfactory staining were excluded from analysis. Of the satisfactory specimens from participants who progressed to lung cancer, two thirds (14 of 22) showed positive reactivity with the antibody (sensitivity 64%). In contrast, of those that did not progress to lung cancer, 35 of 40 (specificity 88%) did not stain. The likelihood that a premalignant specimen from a participant who would ultimately develop lung cancer would stain with either the SCC or NSCC monoclonal antibodies was highly significant (OR=12.25, 95% C.I.= 2.94–55.20, p=0.0001). Even if the unsatisfactory specimens are considered as non-staining (negative) in the analysis, the staining response remains significant (OR=8.87, 95% C.I.=2.32–36.08, p= 0.0004).

TABLE 4

Result of Double-Bridge Immuno Peroxidase Staining of
Monoclonal Ab Surface Markers Applied to the First
Atypical Sputum Specimen Stored by the JHLP

|  | Lung Cancer | No Lung Cancer | Total |
| --- | --- | --- | --- |
| Satisfactory |  |  |  |
| Stain + | 14 | 5 | 19 |
| − | 8 | 35 | 43 |
| Subtotal | 22 | 40 | 62 |
| Unsatisfactory | 4 | 3 | 7 |
| Total | 26 | 43 | 69 |

The staining patterns were then examined separately for the two (SCC,NSCC antibody cell types. Of the five participants whose Papanicolaou smear results showed less than marked atypia but who developed small cell lung cancer, shown in Table 5, all five stained with the small cell antibody. Although not shown in this table, all of the small cell premalignant specimens also stained with the non-small cell antibody (100% positive cross-staining).

TABLE 5

Results of Double-Bridge Immuno Peroxidase Staining
of Monoclonal Ab Surface Markers
Specific for Cell Type

|  | Pap Smear | |
| --- | --- | --- |
|  | < Marked (x2) | > Marked (x2) |
| Small Cell Ab |  |  |
| Total with Small Cell Ca | 5 | 0 |
| Stained | 5 | — |
| % | 100 | — |
| Non Small Cell Ab |  |  |
| Total with Non Small Cell Ca | 9 | 8 |
| Stained | 2 | 7 |
| % | 22 | 88 |

Of the nine participants whose sputum cytology Papanicolaou smear results showed less than marked atypia but went on to non-small cell cancer, as shown in Table 5, only two (22%) stained with the non-small cell antibody. In contrast, when the atypia was marked on two occasions or showed frank cancer, all but one (7 of 8, or 88%) of the non-small cell premalignant specimens stained with the non-small cell antibody. Among these 17 NSCC specimens, only one (a marked atypia) stained with the small cell antibody (6% positive cross-staining).

Review of the eight of 22 false negative atypias (failure to stain) showed that they were collected on an average of 57 months preceding a diagnosis of cancer, as shown in Table 6. In contrast, the true positive specimens (14 of 22 atypias) had been collected approximately 24 months in advance of diagnosis. Those participants who did not develop cancer had been followed for seven to eight years. The duration of this cancer-free period confirms these latter specimens as true negatives.

The hypothesis that Stage I lung cancer could be detected by morphologic changes in sputum cytology, lead to successful resection, and result in a lowered lung cancer mortality was not borne out by the results of the Johns Hopkins Lung Project study. The dual-screen group that received sputum cytology screening plus chest radiography and the radiographically screened group had identical survival and mortality rates. Failures of both detection and intervention contributed to those results. Unfortunately, 51% of the new cancers that arose during the screening period were "interval" or clinical cases neither detected by regular cytologic nor radiographic screening. Furthermore, of the half which were detected, only 57% were sufficiently well localized for surgical intervention, stage I. The survival in the project was also compared to that of earlier studies. The overall age- and smoking-adjusted lung cancer mortality in both dual-screen and control groups was not less than that of unscreened populations. It was concluded, therefore, that there was no mortality benefit associated with the addition of the cytomorphologic screening of sputum to chest films.

Almost two-thirds (147 of 233, or 63%) of the lung cancers in the dual-screen group occurred in those without positive cytomorphology. This observation indicates that compared to the absence of atypia, the presence of morphologic atypia is not a sufficiently sensitive intermediate indicator for the subsequent development of lung cancer. Yet when present, atypia has been shown to be reasonably predictive in reflecting an enhanced risk of developing cancer. Over eight to ten years of screening, 86 of 626 (14%) with at least moderate atypia progressed to lung cancer, compared with 147 cases of lung cancer (3%) which developed among 4600 participants without atypia. Further, all of the different cell types are represented in these atypical specimens. The eventual lung cancer cell types could not be distinguished by separate morphologic characteristics in the pre-malignant atypias. Nevertheless, for the majority of lung cancer cases, pre-malignant morphologic change in sputum cytology was not apparent. This suggests that if examination of exfoliated epithelial cells can provide an intermediate endpoint for early detection, morphologic criteria must be supplemented by other indices.

By design, the first available specimen for each subject which showed at least moderately atypical morphology was stained. Among those with positive immunostaining who eventually developed cancer, the sputum specimen had been collected approximately two years (23.8 months) before the development of clinical lung cancer, as shown in Table 6. In reviewing the data of those who developed cancer but whose specimen failed to stain (false negatives), it was postulated that the average interval of more than four years (57.2 months) between the time of sputum collection and development of lung cancer might have adversely affected the likelihood of antibody binding. It was possible that cell differentiation associated with tumor progression might lead to substantial changes in the membrane glycolipid antigen. It is also possible that the antigen may not have been expressed as early as four years in advance of clinical cancer, but may well have been expressed two years in advance of clinical manifestation of the cancer.

TABLE 6

Average Duration in Months from First Atypical
Sputum Specimen Collection to Development of
Cancer or Last Follow-up

|  | Lung Cancer | No Lung Cancer |
| --- | --- | --- |
| Stain + | 23.8 | 83.8 |
| Stain − | 57.2 | 96.7 |

TABLE 7

Staining Results of Sputum Specimens
with < Marked (x2) Pap Smear Morphology
of Individuals Who Progressed to Non Small Cell Cancer

|  | First° Atypical Specimen | Last* Available Specimen |
|---|---|---|
| Total with Non Small Cell Ca | 9 | 9 |
| Stained | 2 | 8 |
| % | 22 | 89 |

°Average: 40 months prior to cancer
*Average: 26 months prior to cancer

TABLE 8

Result of Double-Bridge Immuno Peroxidase Staining of
Monoclonal Ab Surface Markers Applied to the Most
Recent Atypical Sputum Specimens Stored by the JHLP

|  | Lung Cancer | No Lung Cancer | Total |
|---|---|---|---|
| Satisfactory |  |  |  |
| Stain + | 20 | 5 | 25 |
| − | 2 | 35 | 37 |
| Subtotal | 22 | 40 | 62 |
| Unsatisfactory | 4 | 3 | 7 |
| Total | 26 | 43 | 69 |

Sensitivity = 91%
O.R. = 70
Specificity = 88%
95% C.I. = 10.46 − 297.8
Chi-square = 35.62, $p < 1 \times 10^{-6}$ Of the nine participants with less than marked atypia on at least two occasions who went on to develop non-small cell cancer, only 2 (22%) had positive immunostaining, as shown in Table 5. For these participants, the average interval between sputum specimen collection and lung cancer development was 40 months, as shown in Table 7. More recent specimens from these individuals (average 26 months prior to cancer) were chosen for immunostaining as well. In Contrast to the earlier result, eight of nine (89%) of these latter specimens took up the immunostain. The single specimen that did not stain was technically unsatisfactory. A reconstitution of the sensitivity table, Table 8, shows that all but two of those that progressed to lung cancer within two year stained, i.e., 91% sensitivity. Of those that did not progress to lung cancer, the specificity remained at 88%. Therefore, in addition to the morphologic epithelial cell changes which occur early in only a third of those who develop lung cancer, there appears to be a cell surface marker on exfoliated sputum cells from more than 90% of lung cancer patients that is expressed at least two years in advance of the cancer.

Three participants with marked atypia were followed for a prolonged interval without developing lung cancer, Group III. One of the three remains alive 981 months after his atypical sputum. His atypical sputum specimen failed to take up either the NSCC or SCC immunostains, and has since reverted to normal. A second individual is dead from cardiovascular disease 89 months after his atypical sputum. His sputum specimen also failed to take up the immunostains, and had reverted to normal. The third individual died of colon cancer 86 months after his atypical sputum. His sputum specimen took up the NSCC but not the SCC stain, and had remained moderately atypical at his last examination. These results are consistent, therefore, with the high Mab specificity described above.

The small cell antibodies used in the assays described above did not show binding affinities defined by the (SCC-Antigen Workshop) Cluster antigens, Supra. These antigen sites are preserved after tissue fixation and appear to be more specific than other SCC antigens. The antigen seems to be expressed on a 100 kD glycoprotein present to some degree on other neuroendocrine tumors and only rarely on NSCC tumors. The common pathogenesis of SCC and NSCC from a common pleuripotential stem cell may explain some of the cross-reactivity observed between the different tumor types in the assays performed.

It should be noted that most specimens used remained in storage for from five to eight years. Thus, it is possible that the cellular material could have deteriorated during this period of time. Secondly, the rigor of the specimen homogenization process could have destroyed or altered the antigens on the cell's surface, resulting in complete lack of any staining.

Automated staining procedures will reduce variability and reduce the frequency of technically unsatisfactory slides. Automated quantitation of staining will minimize the possibility of subjectivity in interpretation.

The assays of the present invention are suitable for use in diagnostic kits consisting of antibodies, the bronchial or sputum cells to be tested, and any suitable screening technique, such as immunoassay, immunoprecipitation assay, or immunohistochemistry assays. An outside source of target cells are added to the kit's ingredients. The kit includes a source of antibody for use in the assay and the screening means for the assay.

A typical kit comprises a container means for the monoclonal antibodies, plate or slide means for combining said target cells with the monoclonal antibodies, and a packaging means for combining said container means, said plate or slide means, and said means of detection.

Recognition of the expression of one or more neoplastic antigens in advance of clinical cancer opens several potential therapeutic alternatives. Aggressive selective bronchoscopy and either earlier surgery or laser-phototherapy may be considered for newly detected in-situ or microinvasive cancers. Early detection and local therapy might also be appropriate during therapeutic monitoring of treated lung cancers. The greatest impact upon lung cancer survival might result, however, if nutritional interventions were effective in halting or reversing tumor progression from the premalignant stages potentially detectable by monoclonal antibodies.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

The following deposits were made at the American Type

Culture Collection, 12301 Parklawn Drive, Rockville, Md.: 624H12, Acc. No. HB10479, Jun. 13, 1990; 703D4, Acc. No. HB8301, May 16, 1983; 704A1, HB8302, May 16, 1983.

What is claimed is:

1. A process for screening for the presence of lung cancer in an individual comprising:

1) obtaining a sputum or bronchial fluid sample from said individual;
   2) contacting said sample with at least one pre-selected monoclonal antibody under conditions such that said antibody immunogenically binds with a binding site present in said sample for which binding site said antibody is specific, whereby a complex is formed; and
   3) detecting the presence of said complex; wherein said antibody is pre-selected by the process of:
      i) collecting and preserving sputum or bronchial fluid samples from test individuals in which lung cancer is not detectable by chest x-ray or sputum cytology;
      ii) contacting said preserved samples with monoclonal antibodies that are specific for binding sites differentially expressed on normal versus dysplastic versus neoplastic bronchial cells under conditions such that immunological binding to said binding sites can occur, whereby a complex is formed;
      iii) detecting the presence or absence of said complex resulting from step (ii);
      iv) monitoring said test individuals and determining which of said test individuals subsequently develop lung cancer detectable by chest x-ray or clinical symptoms and which of said test individuals do not subsequently develop lung cancer detectable by chest x-ray or clinical symptoms;
      v) selecting from said antibodies of step (ii) those antibodies that preferentially bind to binding sites present in preserved samples from said test individuals who subsequently develop lung cancer detectable by chest x-ray or clinical symptoms compared to preserved samples from said test individuals who do not subsequently develop lung cancer detectable by chest x-ray or clinical symptoms.

2. A process for screening for the presence of lung cancer which comprises:

a) obtaining sputum or bronchial fluid samples from the respiratory tract of an individual who appears to be free of lung cancer by sputum cytology and chest x-ray;
   b) assaying said samples with monoclonal antibodies which:
      i) are specific for antigens which are differentially expressed on normal bronchial cells versus dysplastic bronchial cells or neoplastic bronchial cells;
      ii) are specific for antigens whose differential expression has been shown to distinguish between samples which contain cancer cells and those which do not by evaluation against control samples, said control samples having been taken from individuals having no evidence of lung cancer by sputum cytology or chest x-ray at the time of sampling, some but not all of whom went on to develop lung cancer evident by chest x-ray and sputum cytology, thereby yielding both positive and negative control samples; and
   c) screening for the binding of the monoclonal antibodies to antigens in the sample.

3. The method of claim 1 or 2 wherein the monoclonal antibody is selected from the group consisting of monoclonal antibody designated 704A1 having ATCC Accession No. HB8302, monoclonal antibody designated 703D4 having ATCC Accession No. HB8301, and monoclonal antibody 624H12 having ATCC Accession No. HB10479.

4. A diagnostic kit for screening for the presence of lung cancer in an individual, comprising:

means for sputum or bronchial fluid or other pulmonary cells induction, a means of detection selected from the group consisting of radioisotopic labels, chromophoric labels, and enzyme labels, monoclonal antibody which is specific for a binding site which is differentially expressed on normal bronchial cells versus dysplastic bronchial cells or neoplastic bronchial cells, the above elements of the kit to be used in conjunction with target cells from sputum, bronchial fluid or other pulmonary cells for testing for binding sites present on target cells, said kit including container means for combining said target cells with said monoclonal antibody.

5. The diagnostic kit of claim 4 wherein said monoclonal antibody is selected from the group consisting of monoclonal antibody designated 704A1 having ATCC Accession No. HB8302, monoclonal antibody designated 703D4 having ATCC Accession No. HB8301 and monoclonal antibody 624 H12 having ATCC Accession No. HB10479.

6. A diagnostic kit for screening for the presence of lung cancer in an individual comprising:

means for sputum or bronchial fluid induction;

a means of detection comprising a biotinylated secondary antibody and a biotinylated tertiary antibody;

monoclonal antibody which is specific for a binding site which is differentially expressed on normal bronchial cells versus dysplastic bronchial cells or neoplastic bronchial cells, the above elements of the kit to be used in conjunction with target cells from sputum, bronchial fluid or other pulmonary cells for testing for binding sites present on target cells, said kit including container means for combining said target cells with said monoclonal antibody.

7. The diagnostic kit of claim 6 wherein said monoclonal antibody is selected from the group consisting of monoclonal antibody designated 704A1 having ATCC Accession No. HB8302, monoclonal antibody designated 703D4 having ATCC Accession No. HB8301 and monoclonal antibody 624H12 having ATCC Accession No. HB10479.

* * * * *

UNITED STATES PATENT AND TRADEMARK OFFICE
CERTIFICATE OF CORRECTION

PATENT NO. : 5,455,159
DATED      : Oct. 3, 1995
INVENTOR(S) : James L. Mulshine, Melvyn S. Tockman, Prabodh K. Gupta, John K. Frost It is certified that error appears in the above-indentified patent and that said Letters Patent is hereby corrected as shown below:

On the title page: Item [73]

"Assignees: The Government of the United States of America as represented by the Secretary of the Department of Health and Human Services; and The Johns Hopkins University, Baltimore, Maryland."

Signed and Sealed this

Ninth Day of July, 1996

Attest:

BRUCE LEHMAN

Attesting Officer     Commissioner of Patents and Trademarks